United States Patent [19]

Santus et al.

[11] Patent Number: 5,165,937
[45] Date of Patent: Nov. 24, 1992

[54] CONTROLLED RELEASE TABLETS CONTAINING FLAVOXATE

[75] Inventors: Giancarlo Santus; Alberto Tajana, both of Milan, Italy

[73] Assignee: Recordati S.A., Chemical and Pharmaceutical Company, Chiasso, Switzerland

[21] Appl. No.: 815,564

[22] Filed: Dec. 26, 1991

Related U.S. Application Data

[63] Continuation of Ser. No. 511,036, Apr. 19, 1990, abandoned.

[30] Foreign Application Priority Data

Apr. 20, 1990 [IT] Italy ............................. 20212 A/89

[51] Int. Cl.$^5$ .................... A01N 43/40; A61K 9/22
[52] U.S. Cl. .................... 424/468; 424/484; 424/486; 424/487
[58] Field of Search ........... 514/320; 546/196; 424/78, 81, 468

[56] References Cited

U.S. PATENT DOCUMENTS

| | | | |
|---|---|---|---|
| 4,428,955 | 1/1984 | Friebe et al. | 514/320 |
| 4,550,115 | 10/1985 | Nordi et al. | 546/196 |
| 4,702,918 | 10/1987 | Ushimaru et al. | 424/461 |
| 4,814,176 | 3/1989 | Makino et al. | 424/468 |

FOREIGN PATENT DOCUMENTS

| | | |
|---|---|---|
| 250374 | 12/1987 | European Pat. Off. . |
| 266707 | 11/1988 | European Pat. Off. . |
| 63-154619 | 6/1988 | Japan . |

*Primary Examiner*—Thurman K. Page
*Assistant Examiner*—Peter F. Kulkosky
*Attorney, Agent, or Firm*—Darby & Darby

[57] ABSTRACT

Solid dosage form for the controlled release of flavoxate hydrochloride is described. The dosage form includes a matrix allowing gradual release of the flavoxate hydrochloride contained within it, a suitable binder which limits the dimensions of the finished solid dosage form, and an acidifying agent which ensures stability of the flavoxate hydrochloride with time and improves its release profile by making it independent of pH.

9 Claims, 1 Drawing Sheet

CONTROLLED RELEASE TABLETS CONTAINING FLAVOXATE

This is a continuation, of application Ser. No. 511,036, filed Apr. 19, 1990, now abandoned.

FIELD OF THE INVENTION

This invention relates to a formulation for controlled release tablets containing as an active ingredient 2,N-piperidinoethyl-3- methylflavone-8-carboxylate hydrochloride, otherwise known as flavoxate hydrochloride and indicated as such hereinafter.

BACKGROUND OF THE INVENTION

Flavoxate hydrochloride is a drug which has long been used therapeutically to limit the symptoms of pollakiuria, particularly nocturia, and of urinary incontinence originating from various pathological situations such as prostatitis, urethritis, cystitis and the side effects of radiotherapy or surgical therapy of the urinary tract. It has also been found that flavoxate is effective in the treatment and diagnosis of erectile impotence.

The therapeutic dose is usually 600–800 mg/day in 3–4 administrations, although in some cases a dose of up to 1200 mg/day has been found more effective. The problem in administering flavoxate hydrochloride derives from the fact that its half life is such that the duration of its therapeutic activity is about 5–6 hours. The short half-life of flavoxate makes it impossible for a patient to ingest a dosage form containing a sufficient amount of the active material in one administration to provide a therapeutic effect while the patient is asleep overnight.

Thus, a formulation able to maintain the therapeutic effectiveness of the drug for a longer duration would reduce the frequency of administration, and thereby considerably improve the quality of life of the patient, especially considering that the therapy using flavoxate is typically long term and prolonged and is particularly directed towards patients of advanced age.

Among all the possible pharmaceutical forms in which flavoxate hydrochloride can be administered, tablets, capsules or pills are the most suitable because they ensure that the exact prescribed quantity of product is taken. In addition, for practical reasons, it is advantageous for the treatment with the drug to take the form of a single tablet or capsule that is administered the smallest possible number of times per day. For example, administration of one tablet per day providing an effective plasma concentration of drug for 24 hours would be ideal.

As far as it is known to the applicant, only Japanese patent application JP 63-154619 and European patent application EP 250374 have confronted the problem of administering flavoxate hydrochloride employing delayed-release formulations. However, even by applying the teachings of these two patent applications, it is not possible to prepare pharmaceutical formulations that can be administered in a single dosage form when the dosage of the active ingredient is very large. In fact, in such cases, the final product would be of such a large size as to be practically unusable.

There is therefore, a need for formulations which provide a large dosage of the active ingredient, and which provide the total requirement for effective treatment, but are of limited size to make ingestion practical.

SUMMARY OF THE INVENTION

According to the present invention such a formulation, having the desired characteristics and also an acceptable finished product size, can be obtained by including the active ingredient in a suitable polymer or mixture of polymers to form a controlled-release system, and adding to this system a suitable binder. The essential purpose of the binder is to maintain the dimensions of the finished product within predetermined limits.

A solid dosage form for the controlled release of flavoxate hydrochloride is described. The dosable form includes a matrix allowing gradual release of the flavoxate hydrochloride contained within it, a suitable binder which limits the dimensions of the finished solid dosable form, and an acidifying agent which ensures stability of the flavoxate hydrochloride with time and improves its release profile by making it independent of pH.

DETAILED DESCRIPTION OF THE INVENTION

Figure 1:
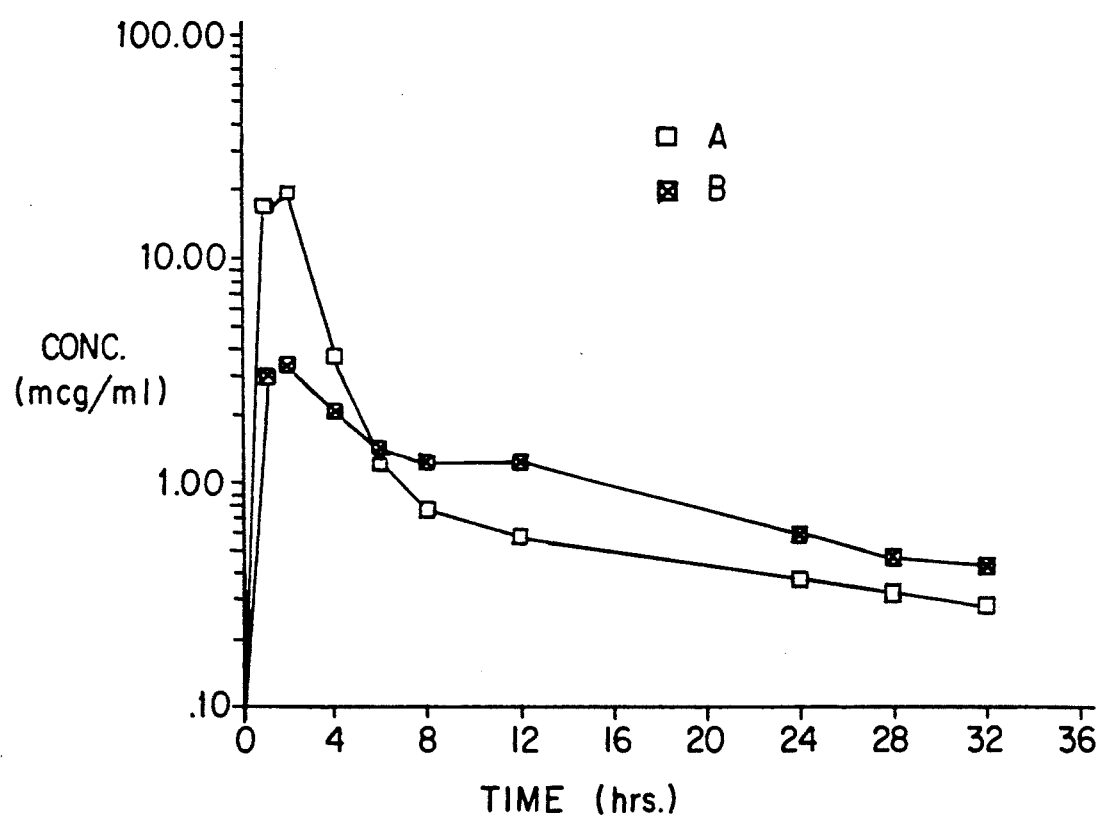
FIG. 1 shows a graph of plasma concentration over time for two different drugs.

The basic characteristic of the present formulation is the presence of the active ingredient in mixture with polyvinyl alcohol (PVA) and a hydrophilic polymer derived from cellulose such as hydroxy-propylmethyl cellulose (HPMC), in accordance with the known technique of preparing hydrophilic matrices swellable in an aqueous environment.

Pharmaceutical tablets using hydrophilic matrices control drug release as follows. After exposure to aqueous fluids, the tablet surface becomes wet and the polymer starts to partially hydrate, forming a gel layer on the matrix surface. The drug contained within the matrix then dissolves and diffuses through the gel barrier. As water permeates into the tablet, the gel layer increases in size. Concomitantly, the outer layers of the tablet become fully hydrated and dissolve, allowing water to penetrate to the tablet core, until the tablet is fully dissolved.

The active ingredient flavoxate hydrochloride (available from Recordati, SpA, Milano, Italy) is basically non-compressible, so use of traditional binders such as gelatine, starch-water, and the like, would imply an excipient/active ingredient ratio such that the finished product would certainly exceed a commercially acceptable overall size. PVA is a strong binder compared with traditional binding agents, and can be successfully used with a very small amount of excipients. Thus, use of PVA makes large-scale use of excipients unnecessary, thus enabling the tablet dimensions to be limited. Furthermore, a characteristic of this formulation is that, because of the materials used, the dissolution profile of flavoxate hydrochloride is not affected by the compression strength. This can be considered a remarkable advantage because this makes the manufacturing procedure safe and relatively easy.

In its unsalified form, flavoxate is not very soluble, and it is advantageous to keep it salified while it is present in the intestinal environment, where there is a tendency for gradual desalification to occur due to the basic pH of the intestinal environment. Moreover, it is known (Arzneim. Forsch. 25, 1707 (1975)) that in a pH 7.4 phosphate buffer, the half-life of flavoxate hydrochloride is about one hour.

It has been found that by introducing into the tablet composition, a suitable stable substance of acid character in appropriate quantities, an acid microenvironment is created about and within the pharmaceutical form.

In addition to favoring stability of the active ingredient, this microenvironment maintains optimum conditions for the external diffusion of the active ingredient even when the external environment has the inherent basic conditions of the intestinal tract. Substances particularly suitable for this purpose have been found to be tartaric acid or citric acid.

Specifically, the present invention comprises tablets for the controlled release of flavoxate hydrochloride composed of:

(a) Flavoxate hydrochloride as active ingredient.

(b) A polymer or mixture of polymers which create a matrix allowing gradual release of the active ingredient contained within the matrix. The polymer or polymers which can be used for this purpose are generally any type of natural or synthetic polymer able to swell on contact with water. Such polymers include: methylcellulose of various molecular weights, polyvinyl alcohols, acrylic copolymers and hydroxypropyl methylcellulose (HPMC). It is generally possible use a polymer quantity within 5 and 10% by weight of the total weight of the finished formulation. HPMC (Methocel K15M) (from Colorcon, Orpinton Kent, U.K.) is particularly preferred, in a 1:10 w/w ratio to the active ingredient.

(c) A suitable binding agent such as polyvinylpyrrolidone (PVP), cellulose or PVA (from Nippon Gohsei, Osaka, Japan), generally in a quantity of between 1% and 5% of the total weight of the formulation. PVA is preferably used in a 1:20 w/w ratio to the active ingredient, thus ensuring the formation of a tablet of acceptable technological dimensions such as to favor the compliance of the patient.

(d) A suitable acidifying agent for maintaining the solubility of the active ingredient even in a basic environment while at the same time favoring its stability. Suitable substances include tartaric acid, citric acid, phosphates and the like. Tartaric acid (from Bracco, Milano, Italy) or citric acid is preferred in a 1:8 w/w ratio to the active ingredient.

(e) A suitable lubricant system to enable the tablets to be produced on high-speed presses. The lubricant can be a common lubricant known in the art. A talc/magnesium stearate mixture (magnesium stearate from Unione Chimica Europea, Milano, Italy and talc from Tradeco, Milano, Italy) is preferred in freely variable proportions, provided that the total weight of the mixture is within 1–3% by weight of the finished product.

(f) Optionally, to improve the palatability of the tablet (given the bitter taste of flavoxate hydrochloride), the tablet can be coated, following known methods, with suitable substances. These substances, which must in any event be readily soluble and not affect the release characteristics, can be chosen either from aqueous coatings or non-aqueous coatings.

The tablets of the present invention can be produced by common presses in accordance with the known art as described in greater detail in the following examples. Capsules and other solid dosage forms may also be formed according to the present invention.

Stability data at room temperature confirm a good stability of flavoxate hydrochloride with unchanged dissolution patterns of the tablets. In the following examples, reference is made to the results obtained using the tablets. The purpose of these examples is to better illustrate the invention and to show its advantages and applicability but without in any way constituting a limitation thereon.

EXAMPLE 1

A standard percentage composition and preparation method is described for controlled release tablets containing 400, 600 and 800 mg of flavoxate HCl as active ingredient.

| Composition | % by weight | weight for batch |
|---|---|---|
| Flavoxate HCl | 76.9 | 3076 g |
| Hydroxypropylmethylcellulose (Methocel K15M) | 7.7 | 308 g |
| Polyvinyl alcohol | 3.8 | 152 g |
| Magnesium stearate | 0.8 | 32 g |
| Tartaric acid | 9.6 | 384 g |
| Talc | 1.2 | 48 g |

Preparation Method

The dry flavoxate HCl and hydroxypropylmethylcellulose were mixed together using a High Speed Mixer DIOSNA P25 from Dierks and Sohne, Osnabruck, Germany, and then made into a paste by adding aqueous polyvinyl alcohol solution. The paste was granulated using a Wet Granulator FGS from Erweka Apparatebau GmbH, Heusenstamm, Germany, and dried to a water content of less than 3%, using a Buhler Oven at 50° C. for 3 hours. The granulate was then mixed with tartaric acid, talc and magnesium stearate. Alternatively, the tartaric acid can be added at the beginning, directly into the paste to be granulated.

The mixture was then compressed with a rotary press (AM 13/8, from Ronchi, Cinisello B. Milano, Italy) fitted with suitable punches to produce tablets. The total finished weight of the tablets containing 400, 600 and 800 mg of active ingredient, was 520.1, 780.2 and 1040.3 mg, respectively.

EXAMPLE 2

To improve palatability, the tablets obtained by the method described in Example 1 can be coated by known methods with a solution having the following composition:

| Composition | % by weight |
|---|---|
| Methocel E 5 (HPMC) | 5.7 |
| Talc | 7.4 |
| Titanium dioxide | 5.0 |
| Saccharose | 1.1 |
| Polyethylene glycol 6000 | 1.1 |
| Water | 79.6 |

Coating Procedure

The coating solution, which provides a completely water-soluble coating, was sprayed into a rotating pan (model MC/25 of Pellegrini, Vimodrone, Milano, Italy) onto the tablets preheated to 45° C. During the process the drying air temperature was maintained at 70° C. and the temperature of the tablets maintained at 50° C. to ensure good water evaporation.

To demonstrate characteristics of the above formulation, data are provided regarding in vitro tablet dissolution tests. These data emphasize the independence of the formulation from the pH of the medium, its stability and the independence from the compression strength. An in vivo study on the blood plasma levels prevailing after ingestion of the tablets is also provided.

EXAMPLE 3

Dissolution

The cumulative dissolution of the tablets was investigated in vitro using the apparatus II of U.S. Pharmacopoeia XXI Ed. The apparatus used was a Dissolutest Prolabo with six standard U.S. Pharmacopoiea vessels. One tablet to be dissolved was placed in each of the six vessels. As a dissolution medium (a) 900 ml of 0.1 N HCl and (b) 900 ml of pH 7.4 phosphate buffer, respectively were used. The temperature was maintained at 37° C. and the rotational speed of the paddle at 60 rpm. Samples of 10 ml were withdrawn every hour and the percentage dissolution was determined by U.V. spectrophotometry, reading the absorbance at 291 nm.

Tables 1 and 2 show the experimental results expressed as cumulative percentage of substance dissolved per unit of time under various conditions, related to the quantity of substance initially present. The dissolution of tablets respectively containing 400 mg (A) and 600 mg (B) of active ingredient and furthermore both containing tartaric acid in their formulation, is compared with the dissolution of tablets containing 400 mg (C) of active ingredient having no acidifying agent in the formulation.

As can be seen from the data, the presence of the acidifying agent in the tablets renders the dissolution independent from the pH of the dissolving medium and in particular improves the dissolution of the active ingredient at pH 7.4 (Table 2, formulations A or B vs. C).

TABLE 1

| | Cumulative dissolution in 900 ml 0.1N HCl | | |
|---|---|---|---|
| Time hours | A % ($\pm$s.d.) | B % ($\pm$s.d.) | C % ($\pm$s.d.) |
| 1 | 3.95 (0.42) | 5.55 (0.26) | 5.03 (0.22) |
| 2 | 8.22 (1.01) | 9.69 (0.54) | 6.61 (0.36) |
| 3 | 13.21 (1.58) | 15.50 (0.91) | 11.89 (0.52) |
| 4 | 18.20 (2.12) | 20.50 (0.94) | 15.98 (0.82) |
| 5 | 22.94 (2.57) | 26.11 (1.25) | 20.32 (1.13) |
| 6 | 27.68 (3.06) | 31.63 (1.64) | 24.70 (1.00) |
| 7 | 32.42 (3.60) | 36.60 (1.54) | 29.80 (1.58) |
| 8 | 38.63 (4.13) | 42.03 (1.28) | 33.13 (1.76) |

TABLE 2

| | Cumulative dissolution in 900 ml phosphate buffer pH 7.4 | | |
|---|---|---|---|
| Time hours | A % ($\pm$s.d.) | B % ($\pm$s.d.) | C % ($\pm$s.d.) |
| 1 | 6.15 (0.36) | 8.28 (0.59) | 1.12 (0.19) |
| 2 | 14.24 (1.08) | 18.43 (0.55) | 1.39 (0.23) |
| 3 | 19.73 (1.47) | 26.58 (0.61) | 2.25 (0.24) |
| 4 | 28.52 (2.17) | 34.08 (0.58) | 2.38 (0.28) |
| 5 | 32.20 (2.71) | 39.74 (1.80) | 2.72 (0.26) |
| 6 | 41.02 (1.85) | 48.25 (1.97) | 3.19 (0.36) |
| 7 | 44.67 (2.64) | 51.46 (2.25) | 3.66 (0.31) |
| 8 | 48.15 (2.82) | 53.31 (4.35) | 3.84 (0.37) |

EXAMPLE 4

Influence of Compression Strength on Dissolution

Tablets having the composition described in Example 1 were compressed using an instrumented rotary press (AM 13/8 of Ronchi, Cinisello B. Milano, Italy) at three different compression strengths of: 5 kN (D), 10 kN (E), 16 kN (F). The press was equipped with strain gauges to measure both the forces exerted by upper and lower punches and the ejection force. The analyzing recorder was a 3655 E Recorder of Yokagawa.

TABLE 3

| | Cumulative dissolution in 900 ml 0.1N HCl | | |
|---|---|---|---|
| Time hours | D (5 kN) % ($\pm$s.d.) | E (10 kN) % ($\pm$s.d.) | F (16 kN) % ($\pm$s.d.) |
| 1 | 8.61 (1.10) | 8.01 (1.17) | 7.97 (0.88) |
| 2 | 13.97 (0.95) | 15.43 (1.32) | 13.46 (1.98) |
| 3 | 18.29 (1.47) | 19.88 (1.15) | 19.21 (1.58) |
| 4 | 22.66 (1.46) | 24.34 (1.40) | 25.15 (2.91) |
| 5 | 28.83 (1.41) | 31.87 (1.51) | 30.69 (1.87) |
| 6 | 34.93 (1.68) | 39.45 (2.97) | 36.24 (4.09) |
| 7 | 39.49 (0.98) | 44.94 (1.89) | 41.25 (3.59) |
| 8 | 44.04 (1.87) | 50.42 (3.71) | 46.26 (4.14) |

As can be seen, the compression strength does not affect the dissolution profile of flavoxate hydrochloride from this formulation.

EXAMPLE 5

Stability

The dissolution of tablets having the composition described in Example 1 and containing 600 mg of active ingredient, was investigated after 1 year storage at room temperature (15°–25° C.) and relative humidity (60–75%).

The corresponding data are reported in Table 4 (solution of 0.1 N HCl) and Table 5 (solution of phosphate buffer pH 7.4) respectively.

TABLE 4

| | Cumulative dissolution in 900 ml 0.1N HCl | |
|---|---|---|
| Time hours | initial % ($\pm$s.d.) | 1 year % ($\pm$s.d.) |
| 1 | 5.55 (0.26) | 4.55 (0.25) |
| 2 | 9.69 (0.54) | 8.28 (0.87) |
| 3 | 15.50 (0.91) | 13.52 (1.52) |
| 4 | 20.50 (0.94) | 18.84 (2.14) |
| 5 | 26.11 (1.25) | 24.29 (2.77) |
| 6 | 31.63 (1.64) | 29.41 (2.26) |
| 7 | 36.60 (1.54) | 34.86 (2.69) |
| 8 | 42.03 (1.28) | 39.82 (2.69) |

TABLE 5

| | Cumulative dissolution in 900 ml phosphate buffer pH 7.4 | |
|---|---|---|
| Time hours | initial % ($\pm$s.d.) | 1 year % ($\pm$s.d.) |
| 1 | 8.28 (0.59) | 6.23 (0.43) |
| 2 | 18.43 (0.55) | 16.89 (0.82) |
| 3 | 26.58 (0.61) | 24.78 (1.01) |
| 4 | 34.08 (0.58) | 31.98 (1.23) |
| 5 | 39.74 (1.80) | 38.14 (2.05) |
| 6 | 48.25 (1.97) | 46.54 (2.15) |
| 7 | 51.46 (2.25) | 49.98 (2.56) |
| 8 | 53.31 (4.35) | 52.04 (2.84) |

As can be seen, in both cases there is no difference between initial and 1 year data at two different pH values.

EXAMPLE 6

Blood Plasma Levels

A cross-over trial was carried out in two periods using a single dose. The trial was conducted on 6 healthy adult volunteers who had received a 400 mg controlled release tablet of flavoxate hydrochloride formulated as described in Examples 1 and 2, or as reference, two 200 mg flavoxate hydrochloride tablets in the currently commercially available formulation (Genurin SF) (Recordati SpA, Milano, Italy). The plasmatic concentration of the principal metabolite of flavoxate, namely 3-methylflavone-8-carboxylic acid (MFCA), was then measured.

FIG. 1 shows the mean MFCA plasmatic levels attained in the trial. The vertical axis represents concentration in mcg/ml and the horizontal axis represents time in hours. The curve indicated by A represents the levels attained after administering Genurin SF, while the curve indicated by B represents the levels attained after administering the controlled release formulation.

From FIG. 1 it can be seen that when the active ingredient is administered by means of the tablets formulated in accordance with the present invention, the duration of therapeutically effective levels of flavoxate is much longer (mean value 11.35 hours for curve B and 6.74 hours for curve A at plasma concentrations greater than or equal to 1 mcg/ml, this being the minimum effective value).

What is claimed is:

1. A solid dosage form for the controlled release of a therapeutically effective amount of a flavoxate salt, said solid dosage form comprising:
    a) a flavoxate salt;
    b) a polymer mixed with said flavoxate to form a controlled release matrix, said polymer selected from the group consisting of methylcellulose, acrylic copolymers and hydroxypropylmethyl-cellulose;
    c) a binding agent mixed with said matrix, said binding agent present in a ratio of about 1:20 by weight to said flavoxate salt, and said binding agent selected from the group consisting of polyvinylpyrrolidone, cellulose and polyvinyl alcohol; and
    d) an acidifying agent mixed with said matrix, said acidifying agent selected from the group consisting of citric acid and tartaric acid, said acidifying agent rendering the dissolution of the dosage independent of the pH of the dissolving medium said matrix divided into individual dosage forms, such that each dosage contains a therapeutically effective amount of flavoxate salt.

2. The solid dosage form of claim 1, wherein said hydroxypropylmethylcellulose polymer is present at a ratio of 1:10 by weight to the flavoxate salt.

3. The solid dosage form of claim 1, wherein said acidifying agent is present at a ratio of about 1:8 by weight to the flavoxate salt.

4. The solid dosage form of claim 1, wherein each individual dosage form is coated with a water-soluble film and wherein the dissolution of the dosage is not affected by said film.

5. The solid dosage form of claim 4, wherein said water-soluble film and wherein the dissolution of the dosage is not affected by said film comprises hydroxypropylmethylcellulose.

6. The solid dosage form of claim 1, wherein said flavoxate salt is flavoxate hydrochloride.

7. The solid dosage form of claim 6, wherein each individual dosage form contains from about 400 to 1200 mg of flavoxate hydrochloride.

8. The solid dosage form of claim 1, wherein said solid dosage form is a tablet.

9. A controlled release tablet of a therapeutically effective amount of flavoxate hydrochloride, said tablet comprising:
    a) flavoxate hydrochloride;
    b) hydroxypropylmethylcellulose mixed with said flavoxate to form a controlled release matrix;
    c) polyvinyl alcohol mixed with said matrix; and
    c) an acidifying agent selected from the group consisting of citric acid and tartaric acid, said agent mixed with said matrix and said acidifying agent rendering the dissolution of the dosage independent of the pH of the dissolving medium, said matrix divided into individual dosage forms and compressed into tablets, such that each tablet contains a therapeutically effective amount of flavoxate hydrochloride.

* * * * *

UNITED STATES PATENT AND TRADEMARK OFFICE
CERTIFICATE OF CORRECTION

PATENT NO. : 5,165,937

DATED : November 24, 1992

INVENTOR(S) : Giancarlo Santus; Alberto Tajana

It is certified that error appears in the above-identified patent and that said Letters Patent is hereby corrected as shown below:

item                  <u>Title Page</u>
[30]  Foreign Application Priority Data

Apr. 20, 1989  [IT] Italy........................20212 A/89

Signed and Sealed this

Ninth Day of November, 1993

Attest:

BRUCE LEHMAN

*Attesting Officer*   *Commissioner of Patents and Trademarks*